United States Patent [19]
Larsson et al.

[11] Patent Number: 5,985,835
[45] Date of Patent: *Nov. 16, 1999

[54] DESMOPRESSIN FOR NOCTURIA, INCONTINENCE AND ENURESIS

[75] Inventors: Krister Larsson; Thomas Mellbrand, both of Malmö ; Birgitta Mörnstam, Bunkeflostrand; Jan Roschester, Lund; Jan-Ake Sköldback, Malmö ; Ragner Asplund, Strimsund, all of Sweden; Jens-Peter Nørgaard, Copenhagen, Denmark

[73] Assignee: Ferring B.V., Hoofddorp, Netherlands

[ * ] Notice: This patent is subject to a terminal disclaimer.

[21] Appl. No.: 08/924,459

[22] Filed: Jul. 13, 1997

Related U.S. Application Data

[63] Continuation-in-part of application No. 08/797,826, Feb. 10, 1997, Pat. No. 5,763,407, which is a continuation of application No. 08/524,761, Sep. 7, 1995, Pat. No. 5,674,850, which is a continuation of application No. 08/176,411, Dec. 23, 1993, abandoned.

[51] Int. Cl.$^6$ .......... A61K 38/00; A61K 38/02; C07K 5/00; C07K 7/00
[52] U.S. Cl. .............. 514/16; 514/15
[58] Field of Search ............ 514/15, 16; 530/315, 530/328

[56] References Cited

U.S. PATENT DOCUMENTS

| | | | |
|---|---|---|---|
| 5,674,850 | 10/1997 | Larsson et al. | 514/16 |
| 5,763,407 | 6/1998 | Larsson et al. | 514/16 |

*Primary Examiner*—Avis M. Davenport
*Attorney, Agent, or Firm*—Hopgood, Calimafde, Kalil & Judlowe

[57] ABSTRACT

A process for the manufacture of high purity desmopressin produced in single batches of substantial size and a method of treating nocturia, incontinence and enuresis with the high purity desmopressin produced therefrom.

5 Claims, 1 Drawing Sheet

DESMOPRESSIN FOR NOCTURIA, INCONTINENCE AND ENURESIS

RELATED CASES

This is a continuation-in-part of application Ser. No. 797,826 filed Feb. 10, 1997 now U.S. Pat. No. 5,763,407 which is a continuation of Ser. No. 524,761 filed Sep. 7, 1995, now U.S. Pat. No. 5,674,850, which is a continuation of Ser. No. 176,411 filed Dec. 23, 1993, which is abandoned.

FIELD OF THE INVENTION

The present invention relates to high-purity desmopressin produced in single batches of substantial size, and to the use of such high-purity desmopressin in methods of treating nocturia, incontinence and enuresis.

BACKGROUND

The hormone analog 1-deamino-8-D-arginine vasopressin (desmopressin, hereinafter also abbreviated "DDAVP") is an important medicine for the treatment of diurea, such as associated with diabetes insipidus and nocturnal enuresis, and urine incontinence, and for the treatment of bleeding disorders such as hemophilia A, von Willebrand's disease and other conditions associated with platelet dysfunction.

Medium-size peptides can be routinely produced by a variety of multi-step techniques in moderately pure form. Their impurity pattern and, thus, measures to be taken for their purification depend on the purity of reactants and reagents, the particular route of synthesis and reaction conditions in general.

This further purification, however, often requires highly efficient purification methods, such as electrophoresis, or other methods which can only handle small amounts of peptide in a single run. Extensive purification also has a tendency to reduce yield, particularly when applied in the final synthetic steps.

These considerations also apply to the synthesis of DDAVP, which is usually isolated and medically used in form of its acetate. While single batches of pure DDAVP thus may be obtained by use of conventional methods of synthesis and purification, the scale in which single batches of DDAVP can be prepared by these methods is unsatisfactory from an economic standpoint. In this specification, the term "single batch of DDAVP" signifies the DDAVP obtained in one single final step of DDAVP synthesis and purification. In view of the complexity of synthesis of DDAVP and other medium-size peptides, and also because of their often extremely high biologic activity, such single batch of substantial size is a batch containing product in the order of 500 g.

As rule, single DDAVP batches differ in, i.e., DDAVP-content and pattern of impurities. Documentation requirements for single batches, no matter whether small or large, include DDAVP-assay and tests such as specific optical rotation, absorbance, amino acid composition, content of related peptides, acetic acid and water. Since cost for analysis is substantial and identical for batches of all sizes, the production of DDAVP in single batches of substantial size, and DDAVP thus produced is desirable. There is, of course, also the usual benefit of economics of scale in producing high-purity DDAVP in single batches of substantial size.

OBJECTS OF THE PRESENT INVENTION

Accordingly, it is an object of the present invention to provide large single batches of high-purity DDAVP.

It is another object of the invention to provide an economical process by which large-size single batches of high-yield, high-purity DDAVP can be prepared.

It is a further object of the invention to provide a method of treating nocturia, incontinence and enuresis by administration of an adequate dose of DDAVP obtained from such single large batches.

SUMMARY OF THE INVENTION

In accordance with the present invention, there are provided single batches of desmopressin of at least 50 g, preferably at least 100 g, particularly preferred of at least about 500 g in weight, containing respectively no less than 44 g, preferably 88 g, particularly preferred about 440 g (95.0% by weight) of $C_{46}H_{64}N_{14}O_{12}S_2$, and a process for producing the same. Also provided are single batches of desmopressin having a weight of at least about 50 g, preferably 100 g, particularly preferred about 5000 g, containing no less than 98.5% by weight of desmopressin in respect of adjoining matter other than acetic acid and water, and a process for producing the same. The desmopressin batches according to the invention thus do not contain more than a total of 1.5% by weight of adjoining matter other than water and acetic acid, i.e. no more than 1.5% by weight of impurities. Acetic acid is chemically bound to the basic desmopressin, which is provided by the inventive process as an acetate of varying stoichiometry. Desmopressin batches according to the invention also contain small amounts of water which only can be removed with difficulty. Such adjoining acetic acid or water do not impair the pharmacological properties of desmopressin. Such high-purity desmopressin batches, therefore, will usually contain a total of at least about 3,5% weight of acetic acid and water.

The inventive process is characterized by comprising a final synthetic step, in which at least 100 g, preferably 200 g, particularly preferred at least about 500 g, of $R^1$-mercaptopropionyl-Tyr-Phe-Gln-Asn-Cys($R^2$)-Pro-D-Arg-Gly-$NH_2$ (SEQ ID NO: 1), $R^1$ and $R^2$ being, independently of each other, selected from acetamidomethyl and triphenylmethyl, are dissolved in a proctic solvent at neutral or slightly acidic conditions to form a reactant solution, a second solution of iodine in a proctic solvent is introduced into said reactant solution under agitation, resulting in a reactant/reagent solution, the amount of iodine being at least about stoichiometric in respect of said $R^1$-mercaptopropionyl-Tyr-Phe-Gln-Asn-Cys($R^2$)-Pro-D-Arg-Gly-$NH_2$ (SEQ ID NO: 1), a disulfide moiety-forming reaction is supported in said admixture until substantially complete formation of desmopressin, wherein said temperature of said admixture is not allowed to exceed 50° C., thus forming a pre-purified solution of desmopressin; the pre-purified desmopressin solution is applied to a separation column containing cation exchange resin equilibrated with acid and desmopressin is eluted; the eluted, at least 98.5% pure (in respect of adjoining matter other than water and acetic acid) desmopressin is isolated in a single batch weighing at least 50 g, preferably at least 100 g, particularly preferred at least 500 g, containing, in addition to minor amounts of acetic acid and water, no less than, respectively, 44 g, 88 g, and 440 g of $C_{46}H_{64}N_{14}O_{12}S_2$ and no more than, respectively, 660 mg, 1,32 g, and 6,6 g of impurities, i.e. adjoining matter other than water and acetic acid.

It is preferred for the derivative of 1-mercaptopropionyl-Tyr-Phe-Gln-Asn-Cys-Pro-D-Arg-Gly-$NH_2$ (SEQ ID NO: 1) to be β-acetamido-metylmercaptopropionyl-Tyr-Phe-Gln-Asn-Cys-(S-acetamido-methyl)-Pro-D-Arg-Gly-$NH_2$ (SEQ ID NO: 1).

It is preferred to elute desmopressin with a buffered solution, particularly with a buffered solution comprising ammonium acetate/acetic acid.

If desired, the at least 95% pure desmopressin obtained by the process according to the invention may be further purified by conventional means, such as electrophoresis, gel permeation chromatography, chromatography, including reverse-phase chromatography, etc. Further purification by gel permeation chromatography and/or reverse phase chromatography is preferred.

At about ambient temperature the cation exchange resin should be substantially stable in contact with iodine dissolved in protic solvents. Preferred resins are based on cross-linked agarose substituted with methylsulfonyl groups, such as S-Sepharose® FF.

Furthermore, the invention discloses desmopressin with a purity of at least 98.5% in respect to other adjoining matter than acetic acid and water, i.e. with a content of impurities of less than 1.5%, produced in batches of at least 50 g, preferably of at least 100 g, particularly preferred of at least about 500 g, for use as a medicine, particularly a medicine for the treatment of various urinary disorders, such as diabetes insipidus, incontinence, enuresis and nocturia, and dysfunctions of the coagulative system, such as hemophilia A, von Willebrand's disease, platelet dysfunctions and other bleeding indications. Such batches of high-purity desmopressin may be used for the manufacture of a medicament intended for treatment of the aforementioned medical disorders.

Further features and advantages of the present invention are evident from the drawing, and the description and appended claims, which follow.

DETAILED DESCRIPTION

Figure 1:
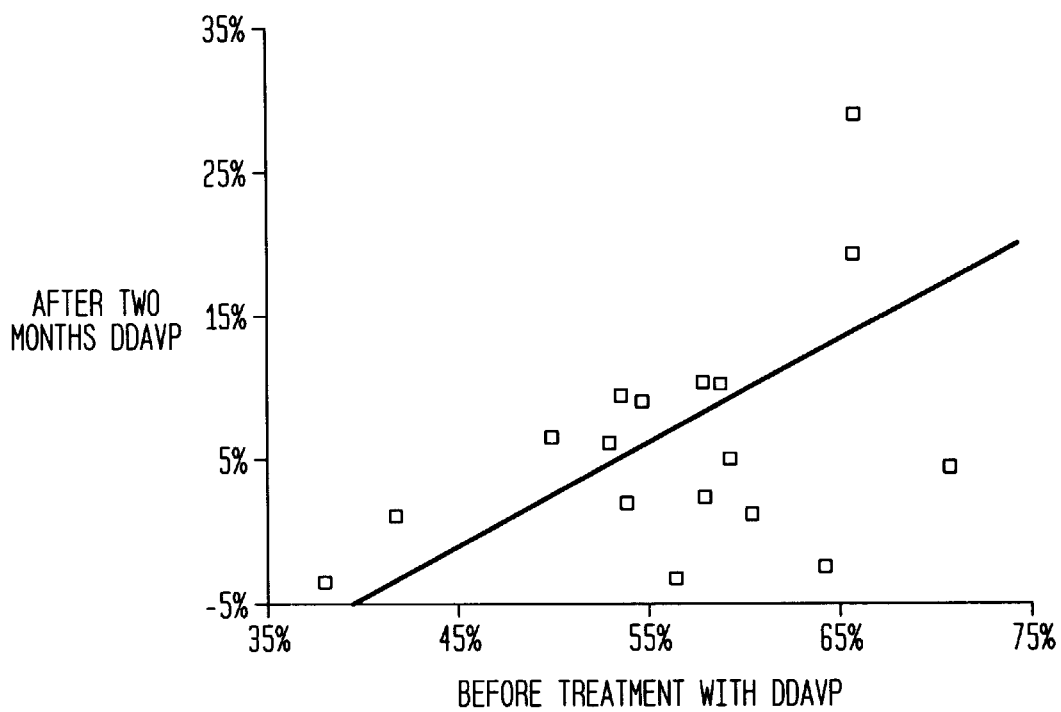
FIG. 1 graphically depicts change in relative amounts of nocturia in a 24-hour period in patients before and after treatment with the present invention.

EXAMPLE 1
Boc-Gln-Asn-Cys(Acm)-Pro-OH (X)

BocCys(Acm)ONp is prepared from BocCys(Acm)OH (Novabiochem, Läufelingen, CH) and p-nitrophenol by reaction with N,N'-dicyclohexylcarbodiimide (DCC) in ethyl acetate and used without purification for the preparation of Boc-Cys(Acm)-Pro-OH (XII) by reacting it with Hpro-OH in DMF/ethyl acetate/HCl at 0° C. while keeping pH neutral by addition of $ET_3N$. Yield 81%. Purity >95% (TLC). Boc-Asn-Cys(Acm)-Pro-OH (XIII) is obtained by deblocking XII in Hcl/HOAc at room temperature, dissolving the thus obtained raw Hcys(Acm-Pro-OH.HCl in DMF and neutralizing it with $ET_3N$, and adding Boc-Asn-ONp (Novabiochem, Läufelingen, CH) at –5° C. while keeping pH neutral. XIII is isolated in 81% yield. $[\alpha]_D^{20}$=–89.70 (1 g/100 ml $H_2O$)

EXAMPLE 2
Mpa (Acm)-Tyr-Phe-$NHNH_2$ (XI)

Mpa(Acm)-Tyr-OEt (XIV) is prepared by reacting H-Tyr-OEt.HCl with Mpa (Acm)-OH (Bahem AG, CH) and DCC in DMF containing 1-hydroxybenzotriazole (HOBt) at 0° while maintaining pH at 7 ($Et_3N$). Yield 48%. The hydrazide XI is prepared by reacting the ester XIV with H-Phe-$N_2H_3$ in DMF/$H_2O$ under catalysis by α-chymotrypsin. Yield 90%; m.p. 240–242° C.

EXAMPLE 3
Mpa(Acm)-Tyr-Phe-Gln-Asn-Cys(Acm)-Pro-OH (SEQ ID NO: 1) (VII).

Boc-Gln-Asn-Cys(Acm)-Pro-OH (X; 600 g) is dissolved in 56 ml trifluoroacetic acid (TFA) which is evaporated after being kept for one hour at room temperature. The residue is dissolved in 970 ml dimethyl formamide (DMF) and cooled, and pH is adjusted to 7 ($ET_3N$). Mpa (Acm)-Tyr-Phe-$NHNH_2$ (XI; 564 g) is dissolved in 5.9 l DMF, the solution is cooled to –18° C., HCl/ethyl acetate (810 ml; 3.2 M) is added and the solution is kept at –15° C. Isoamylnitrite (180 ml) is added and the solution is stirred at about –10° C. for 15 min. After cooling to –20° C. pH is adjusted to 7 ($ET_3N$). The solution of the deblocked tetrapeptide in DMF is added and the mixture stirred at –5° C. After the reaction is virtually complete (99.5% conversion of the deblocked tetrapeptide as determined by TLC), precipitated salt is filtered off and the volume reduced to 3.1 ml by evaporation in vacuo. EtOH (99.5%; 215 ml) is added and the solution heated to 60° C. After cooling to ambient temperature pH is adjusted to 2.5 (conc. HCl). The precipitate is filtered off, washed with 99.5% EtOH, and dried to yield 903 g of white crystals; yield 85%, mp. 188–191° C.

EXAMPLE 4
Boc-D-Arg(HCl)-Gly-$NH_2$ (VIII).

H-Gly-$NH_2$.HCl (168 g) and 1-hydroxy-benzotriazole (HOBt; 213 g) is suspended in 34 ml DMF and the solution is cooled to –10° C. $Et_3N$ (129 ml) is added and the mixture stirred for 15 min. Boc-D-arginine(HCl) (439 g) is added and the temperature brought to 0° C. DCC (290 g) dissolved in 4.5 ml DMF is added and pH adjusted to 6.0 ($ET_3N$). After complete conversion, the formed precipitate is removed by filtration and the filtrate evaporated in vacuo. The residue is dissolved in 5.2 l water, the solution is cooled to 0° C. and pH adjusted to 3 (1M HCl). After removing HOBt by filtration the solution is extracted with dichloromethane. The aqueous phase is reduced to a volume of 1.3 l in vacuo, subjected to azeotropic distillation with butanol (4×), and its volume brought to 4.4 l by addition of butanol. The solution is extracted with 0.1 M HCl containing 10% NaCl (w/w) and 5% butanol (v/v), and thereafter reduced to half its volume by distillation. After repeating the azeotropic distillation with butanol and removing NaCl by filtration, the solution is poured into an eight-fold excess (v/v) of isopropyl acetate, and the precipitate is collected by filtration and washed with isopropyl acetate. Compound VIII was obtained in form of a white amorphous powder; yield 439 g (90%), $[\alpha]_D^{20}$=+4.3° (1 g/100 ml DMF).

EXAMPLE 5
Mpa(Acm)-Tyr-Phe-Gln-Asn-Cys(Acm)-Pro-D-Arg(HCl)-Gly-$NH_2$ (SEQ ID NO: 1) (IX).

BOC-D-Arg(HCl)-Gly-$NH_2$ (VIII; 439 g) is dissolved in 1.5 l acetic acid and 1.3 l HCl/HOAc (2.2 M) is added. After stirring for 1.5 h at room temperature, the solution is evaporated under reduced pressure and the residue dissolved in 1.9 l DMF. The deblocked dipeptide is precipitated in form of oily droplets by adding xylene (2 l). After decantation of the supernatant, the residue is washed with xylene and remaining solvent removed in vacuo. The residue is dissolved in 7.1 l DMF and the solution cooled to –10° C. By addition of $ET_3N$ pH is adjusted to 7.5. Mpa(Acm)-Tyr-Phe-Gln-Asn-Cys(Acm)-Pro-OH (SEQ ID NO: 1) (VII; 903 g) and 129 g HOBt are dissolved in 4.2 l DMF and the deblocked dipeptide H-D-Arg(HCl)-Gly-$NH_2$ in DMF obtained in the preceding step and the calculated amount of DCC is added. After 90% conversion (TLC) DCU is filtered off and the solution reduced to a volume of 6.5 l, heated to 60° C. and poured into 20 l EtOH/EtOAc 85:15 (v/v). The precipitate is collected by filtration and washed with EtOH/EtOAc 85:15. Compound IX was obtained in form of a white powder (yield 1 kg (84.9%), m.p. 182–185° C.) with a purity of 94.5% (HPLC).

EXAMPLE 6

Mpa-Tyr-Phe-Gln-Asn-Cys-Pro-D-Arg-Gly-NH$_2$ (SEQ ID NO: 2) (desmopressin) IX (1 kg) is dissolved in 1,000 l acetic acid/water 1:9 (v/v). The blocked nonapeptide derivative IX is oxidized at room temperature by addition of 200 g iodine dissolved in 8.0 l ethanol by means of a roller pump, the feeding speed of which is being controlled by a UV monitor in order to keep the amount of free iodine in the reaction medium low. Conversion of IX is monitored by HPLC. A yellow color persists after the entire amount of IX has been consumed. The solution from the reaction containing the products is passed through a short stainless steel column containing 160 l S-Sepharose® FF (Pharmacia, Sweden) equilibrated with aqueous acetic acid. The title compound is eluted with 0.08 M NH$_4$Ac/AcOH buffer (24 l, pH 4.1; fractions monitored by HPLC analysis). Fractions containing compound (I) in purity >98.5% (disregarding buffer components) are combined. The solution containing the acetate of pure title compound is concentrated by partial evaporation of solvent in vacuo or by reverse osmosis, and finally freeze dried to obtain a white fluffy powder.

Compound (I) is further purified by gel filtration on Sephadex G25 (0.1 M acetic acid). Elution is followed by analyzing individual fractions with HPLC. The combined fractions containing pure product are combined and freeze dried. Desmopressin (in the acetate form) is obtained in a purity of >98,5% as a white fluffy powder. Yield 440 g.

Peptide-related desmopressin impurities and desmopressin content are determined by HPLC (*Ph. Eur.*, 2nd Ed., p.V.6.20.4). Impurities: Lichrospher RP-18, 5$\mu$(4—4) mm column; loop vol. 20 $\mu$l; flow rate 1.5 ml/min; UV detector at 220 nm; isocratical elution; mobile phase acetonitrile/ 0.067 M phosphate buffer (pH 7.0) 17:83 (v/v). Measurement of peak area; calibration by external standard. Content: same conditions, except for elution by aetonitrile/phosphate buffer gradient varying from 12:88 to 26:74 (v/v).

The experimental procedure describing the production of a batch of about 440 g of high-purity desmopressin has been down-scaled by such adaptation of volumes and weights as being in within the easy reach of a person skilled in the art to produce about 44 g of desmopressin to essentially the same standards of purity.

EXAMPLE 7

This example describes changes in diuresis during a two-month treatment with 40 $\mu$g desmopressin (Minirin®) in a group of elderly persons with increased nocturnal diuresis and decreased ADH secretion. The average age of the men (n=7) was 72±4 years and of the women (n=14) 72±6 years. Nocturnal diuresis decreased after one and two months by 21% and 20% in the men and by 36% and 34% in the women, respectively. Half of the change persisted among the women but not among the men one month after the treatment. The decrease in nocturnal diuresis was greatest among those who, before the treatment, had a large part of their diuresis during the night.

ADH levels were studied in a group of elderly persons who had increased nocturnal diuresis. The levels generally were very low and a pilot study was done to determine the effect of desmopressin treatment during a period of 48 hours.

TABLE 1

| | Desmopressin 40 $\mu$g | | | |
|---|---|---|---|---|
| | 0 | 1 month | 2 months | 3 months |
| Physical examination[a] | x | | x | |
| Urine measurement[b] | x | x | x | x |
| Weight[c] | x | x | x | x |
| Blood tests[d] | x | x | x | x |
| Blood pressure | x | | x | x |
| Questionnaire | x | x | x | x |

[a]Heart-and lung auscultation.
[b]Amount of urine and number of micturitions between 8-20 h and 20-8 h during three successive 24-h periods.
[c]In the morning.
[d]Osmolality, creatinine, natrium and kalium in serum.

The study comprised 27 elderly persons with a recent increase in nocturnal diuresis. They had no cardiac or renal disease or diabetes nor were they receiving diuretics. They had undergone investigation with determination of ADH and ANP in plasma as well as osmolality in serum every fourth hour, beginning at 8.00 a.m. during a 24-hour period. Intravenous specimens for the determination of ADH and NAP were frozen at 18° C. Plasma ADH was measured as arginine vasopressin by radioimmunoassay after extraction with ethanol. The reference range for plasma ADH was 1–5 pmol l$^{-1}$ with an interassay variability of 15.1% at 0.9 pmol l$^{-1}$ and 6.3% at 1.25 pmol l$^{-1}$.

ANP also was taken every fourth hour, beginning at 08.00 h. ANP was measured in the same venous blood specimen as ADH. The determination of plasma ANP was performed radioimmunologically with a rabbit antiserum (A 93, Milab, Malmo, Sweden) at a final dilution of 1:24000. The detection limit is 10 pmol l$^{-1}$. The interassay variation is <10%, and the interassay variation is <5%.

Their nocturnal diuresis had decreased during desmopressin treatment on two successive days. After an evaluation of this study the participants were invited to take part in a two-month treatment with desmopressin (Minirin®) 40 $\mu$g, given as an intranasal aerosol at 20.00 h. The tests consisted of 7 men (aged 72±4 years) and 14 women (aged 73±6 years). No changes in their way of life and no restriction in fluid intake was prescribed. The study was carried out after one and two months of treatment and one month after the treatment.

The subjects underwent clinical examination including blood pressure determination at day 0, 60 and 90. Amount of urine and number of micturitions between 08–20 h and 20–08 h were measured during three successive 24-hour periods starting on day 0, 30, 60 and 90 (Table 1). Mean values of diuresis and micturitions for the 12-hour periods were calculated (Table 2). At these times also a questionnaire with 12 questions about general wellbeing and sleep was filled in (Table 1).

The statistical method used a mean value ± standard deviation. The paired numerical data were analyzed with the 2-sided Student's t-test. Non-numerical data were analyzed with the x'-test.

TABLE 2

Diuresis (ml) during day and night, number of micturitions and
distribution of diuresis before, during and after treatment with desmopressin
Average values for men (n = 6) and women (n = 12)

|  |  | Desmopressin | | | |
| --- | --- | --- | --- | --- | --- |
|  |  | 0 | 1 month | 2 months | 3 months |
| Diuresis-day | Men | 511 ± 85 | 465 ± 72 | 524 ± 117 | 441 ± 68 |
|  | Women | 699 ± 368 | 746 ± 368 | 673 ± 257 | 587 ± 173 |
| Diuresis-day Deviation from initial value % | Men |  | −9 | 2 | −14 |
|  | Women |  | 6 | −4 | −14 |
| Diuresis-night | Men | 763 ± 42 | 603 ± 178 | 612 ± 174 | 717 ± 168 |
|  | Women | 892 ± 361 | 570 ± 172 | 592 ± 124 | 739 ± 260 |
| Diuresis-night Deviation from initial value % | Men |  | −21 | −20 | −6 |
|  | Women |  | −36 | −34 | −17 |
| Diuresis-day/night | Men | 0.67 ± 0.20 | 0.83 ± 0.28 | 0.91 ± 0.29 | 0.66 ± 0.26 |
|  | Women | 0.84 ± 0.40 | 1.46 ± 0.87 | 1.14 ± 0.36 | 0.89 ± 0.36 |
| No. of micturitions - night | Men | 4.3 ± 1.2 | 3.8 ± 1.7 | 4.5 ± 2.0 | 4.1 ± 1.6 |

Before commencing the study, all subjects (n=27) underwent determinations of ADH every fourth hour during a 24-h period. ADH was detectable (>0.4 pmol $l^{-1}$) in 25 of 147 tests (17.0%) among those who wished to participate in the longer-term study (n=21), the corresponding figures for those who did not wish to participate (n=6) being 32 of 42 tests (76.2%) (p<0.0001).

In addition, ANP to exclude heart insufficiency was measured at the same times as ADH. ANP for the men was 56±10 pmol $l^{-1}$ at noon and 64±22 pmol $l^{-1}$ at midnight (NS). The corresponding figures for the women were 83±48 pmol $l^{-1}$ and 71±43 pmol $l^{-1}$, respectively (NS).

Among the men, nocturnal diuresis had decreased by 21% from the initial value after one month and by 20% after two months (Table 2). The corresponding figures for the women were 36% and 34%. For the men an insignificant decrease was still present one month after the last day of treatment, while the women had 17% less nocturnal diuresis at the corresponding time. All the men reduced their nocturnal diuresis by less than 400 ml after both one and two months. For the women, the corresponding figures were 9 and 7 women, respectively. The reduction in the nocturnal diuresis was greatest in those who, before treatment, had a large part of their diuresis during the night (FIG. 1).

Diuresis during the daytime changed insignificantly, but one month after treatment there remained a reduction of daytime diuresis among both men and women. The total 24-hour diuresis was more or less unchanged during the study. The redistribution of diuresis from night to day was more marked in women than in men.

TABLE 3

Blood pressure (mmHg), weight (kg) and osmolality (mosm $l^{-1}$)
in serum for men (n = 6) and women (n = 12)
before, during and after treatment with desmopressin

|  |  | Desmopressin | | | |
| --- | --- | --- | --- | --- | --- |
|  |  | 0 | 1 month | 2 months | 3 months |
| Systolic blood pressure | Men | 153 ± 24 | — | 156 ± 28 | 153 ± 19 |
|  | Women | 160 ± 24 | — | 160 ± 22 | 149 ± 20 |
| Diastolic blood pressure | Men | 83 ± 13 | — | 83 ± 10 | 81 ± 14 |
|  | Women | 87 ± 11 | — | 83 ± 10 | 82 ± 8 |
| Weight | Men | 78 ± 11 | 77 ± 11 | 79 ± 11 | 79 ± 11 |

TABLE 3-continued

Blood pressure (mmHg), weight (kg) and osmolality (mosm $l^{-1}$)
in serum for men (n = 6) and women (n = 12)
before, during and after treatment with desmopressin

|  |  | Desmopressin | | | |
| --- | --- | --- | --- | --- | --- |
|  |  | 0 | 1 month | 2 months | 3 months |
|  | Women | 62 ± 9 | 62 ± 8 | 61 ± 8 | 61 ± 8 |
| Osmolality | Men | 295 ± 5 | 296 ± 10 | 296 ± 9 | 297 ± 3 |
|  | Women | 297 ± 3 | 294 ± 4 | 289 ± 7 | 295 ± 5 |

Body weight did not change during treatment, nor did osmolality, sodium or potassium in serum.

In an unselected group of elderly persons without heart or renal diseases, but: with increased nocturnal diuresis, nocturnal diuresis decreased when desmopressin treatment was given. This group of elderly had low ADH-levels during the 24 hour period, without an increase at night.

The decrease in average diuresis during the night was twice as large in women as in men during the treatment (Table 2). The men's nocturnal diuresis returned to its earlier level within one month after treatment while, among the women, half of the reduction remained one month after treatment. The effect of desmopressin was greatest among those persons who had most nocturnal diuresis. As regards the number of nocturnal micturitions, we also found that the women were affected most positively by the treatment.

EXAMPLE 8

This example provides efficacy and safety data for oral desmopressin in the treatment of increased frequency due to nocturnal polyuria in the elderly. The study started with a run-in week to establish baseline. An open dose titration, one week each of 0.1 mg, 0.2 mg and 0.4 mg, was performed and followed by a wash-out of 1–2 weeks. Then followed the double-blind, placebo controlled, cross-over part of the study using the dose selected in the dose titration. Placebo and active treatment were given for 14 days each in a randomized order.

The study enrolled 24 patients, with 1 control patient who did not receive desmopressin. The diagnosis and main criteria for inclusion was a healthy adult patient between 60–74 years of age suffering from increased nocturnal frequency (≧2 nocturnal voids) and a nocturnal urinary output ≧0.9 ml/min. The desmopressin used for the study was Minirin®, 0.1 mg and 0.2 mg tablets. The duration of treatment was for one week of 0.1 mg, 0.2 mg and 0.4 mg followed by 2 weeks of active treatment of the chosen dose and two weeks of placebo. Study duration, including run-in and wash-out periods, was 9 weeks.

The criteria for evaluation were:
1. Efficacy: the change in nocturnal diuresis (ml/min), nocturnal micturition episodes and 24-hour diuresis.
2. Safety: changes from baseline in blood pressure, S-sodium, ankle circumference and bodyweight. Incidence of adverse events.

The efficacy endpoints during the double blind part of the study were subjected to statistical analysis with an ANOVA model. Sequence effect was tested with the within mean square in the ANOVA. The residuals obtained were plotted against predicted values, normal plots were also produced. The plots were examined for relationship between variance and mean non-normality. Shapiro-Wilks test was performed to assist in these assessments. The difference in effect is presented in 95% confidence intervals for least square means, placebo versus desmopressin. All tests performed used a significance level of $\alpha=5\%$.

In summary, desmopressin gave a lower nocturnal diuresis and fewer nocturnal voids compared to placebo. Both differences were statistically significant. Analysis showed that desmopressin gave significantly longer duration of sleep between voids than placebo. The type and incidence of adverse events judged by the investigator to be related to desmopressin were such as expected, i.e. headache, nausea, vomiting, abdominal pain and hyponatremia. One patient dropped out due to an adverse event. No serious adverse events occurred. None of the adverse events were of severe intensity.

In the present study desmopressin tablets appeared to be well tolerated in the treatment of nocturnal polyuria in elderly heathy men and women. Desmopressin significantly decreases nocturnal symptoms and is well tolerated in an elderly population.

While the exemplary embodiments have been described above, one skilled in the art could readily adapt the exemplary embodiments to ones of equivalent scope having substantially the same function after having the benefit of this disclosure.

What is claimed is:

1. A method for treating nocturia, incontinence and enuresis, comprising oral, nasal or intravenous administration of a dose of desmopressin effective to produce a physiological effect and having a purity of at least 98.5% with respect to adjoining matter other than water and acetic acid, said desmopressin having been produced in single batches of at least 50 g. said desmopressin produced by a process consisting of a final synthetic step, in which at least about 100 g. of mercapto-propionyl-Tyr-Phe-Gln-Asn-Cys-Pro-D-Arg-Gly-NH$_2$ (SEQ. ID NO. 2) or a derivative thereof, said derivative being stable at neutral or slightly acidic conditions, are dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

2. A single oral dose of desmopressin effective to produce a physiological effect for treatment of nocturia, incontinence and enuresis, said dose prepared from a desmopressin batch produced by a process for production of single batches of desmopressin having a weight of at least about 500 g. containing at least 98.5% by weight of desmopressin ($C_{46}H_{64}N_{14}O_{12}S_2$) in respect of adjoining matter other than water and acetic acid, consisting of a final synthetic step, in which at least about 1 kg. of mercapto-propionyl-Tyr-Phe-Gln-Asn-Cys-Pro-D-Arg-Gly-$NH_2$ (SEQ. ID NO. 2) or a derivative thereof, said derivative being stable at neutral or slightly acidic conditions, are dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

3. A single intranasal dose of desmopressin effective to produce a physiological effect for treatment of nocturia, incontinence and enuresis, said dose prepared from a desmopressin batch produced by a process for production of single batches of desmopressin having a weight of at least about 500 g. containing at least 98.5% by weight of desmopressin ($C_{46}H_{64}N_{14}O_{12}S_2$) in respect of adjoining matter other than water and acetic acid, consisting of a final synthetic step, in which at least about 1 kg. of mercapto-propionyl-Tyr-Phe-Gln-Asn-Cys-Pro-D-Arg-Gly-$NH_2$ (SEQ. ID NO. 2) or a derivative thereof, said derivative being stable at neutral or slightly acidic conditions, are dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

4. A single intravenous dose of desmopressin effective to produce a physiological effect for treatment of nocturia, incontinence and enuresis, said dose prepared from a desmopressin batch produced by a process for production of single batches of desmopressin having a weight of at least about 500 g. containing at least 98.5% by weight of desmopressin ($C_{46}H_{64}N_{14}O_{12}S_2$) in respect of adjoining matter other than water and acetic acid, consisting of a final synthetic step, in which at least about 1 kg. of mercapto-propionyl-Tyr-Phe-Gln-Asn-Cys-Pro-D-Arg-Gly-$NH_2$ (SEQ. ID NO. 2) or a derivative thereof, said derivative being stable at neutral or slightly acidic conditions, are dissolved in a protic solvent at neutral or slightly acidic conditions to form a reactant solution into which a second solution of iodine in a protic solvent or solvent mixture is introduced under agitation to form a reactant/reagent solution in which desmopressin is being formed.

5. A single oral dose of desmopressin effective to produce a physiological effect for treatment of nocturia, incontinence and enuresis, said dose prepared from a single batch of desmopressin containing no less than 44 g of desmopressin ($C_{46}H_{64}N_{14}O_{12}S_2$) and no more than a total of 1.5% by weight of adjoining matter with respect to desmopressin ($C_{46}H_{64}N_{14}O_{12}S_2$) other than water and acetic acid.

\* \* \* \* \*

SEQUENCE LISTING (1) GENERAL INFORMATION:

(iii) NUMBER OF SEQUENCES:  2

(2) INFORMATION FOR SEQ ID NO:1:

(i) SEQUENCE CHARACTERISTICS:
      (A) LENGTH:  5 amino acids
      (B) TYPE:  amino acid
      (C) TOPOLOGY:  linear (ii) MOLECULE TYPE: peptide (xi) SEQUENCE DESCRIPTION: SEQ ID NO:1:

Tyr Phe Gln Asn Cys
1               5

(2) INFORMATION FOR SEQ ID NO:2:

(i) SEQUENCE CHARACTERISTICS:
      (A) LENGTH:  6 amino acids
      (B) TYPE:  amino acid
      (C) TOPOLOGY:  linear (ii) MOLECULE TYPE:  peptide (xi) SEQUENCE DESCRIPTION: SEQ ID NO:2:

Tyr Phe Gln Asn Cys Pro
1               5